United States Patent
Shuros et al.

(10) Patent No.: US 11,147,976 B2
(45) Date of Patent: Oct. 19, 2021

(54) LATERAL FIXATION FOR CARDIAC PACING LEAD

(71) Applicant: Cardiac Pacemakers, Inc., St. Paul, MN (US)

(72) Inventors: Allan C. Shuros, St. Paul, MN (US); Arthur J. Foster, Blaine, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 220 days.

(21) Appl. No.: 16/385,935

(22) Filed: Apr. 16, 2019

(65) Prior Publication Data

US 2019/0314636 A1  Oct. 17, 2019

Related U.S. Application Data

(60) Provisional application No. 62/658,417, filed on Apr. 16, 2018.

(51) Int. Cl.
*A61N 1/05* (2006.01)
*A61N 1/375* (2006.01)

(52) U.S. Cl.
CPC ....... *A61N 1/37518* (2017.08); *A61N 1/0573* (2013.01); *A61N 1/37512* (2017.08)

(58) Field of Classification Search
CPC .......................... A61N 1/0573; A61N 607/128
See application file for complete search history.

(56) References Cited

U.S. PATENT DOCUMENTS

| | | | |
|---|---|---|---|
| 4,378,023 A * | 3/1983 | Trabucco | A61B 17/3468 607/120 |
| 4,858,623 A | 8/1989 | Bradshaw et al. | |
| 5,522,875 A | 6/1996 | Gates et al. | |
| 5,571,162 A * | 11/1996 | Lin | A61N 1/0563 607/122 |
| 5,683,447 A | 11/1997 | Bush et al. | |
| 7,860,580 B2 | 12/2010 | Falk et al. | |
| 2003/0204234 A1* | 10/2003 | Hine | A61N 1/057 607/128 |
| 2006/0235499 A1 | 10/2006 | Heil et al. | |
| 2007/0250144 A1 | 10/2007 | Falk et al. | |

FOREIGN PATENT DOCUMENTS

EP  0393265 A1  10/1990

* cited by examiner

*Primary Examiner* — George R Evanisko
(74) *Attorney, Agent, or Firm* — Faegre Drinker Biddle & Reath LLP (57) ABSTRACT

Various aspects of the present disclosure are directed toward apparatuses, methods and systems that include implantable lead. The implantable lead may include an electrode arranged and a fixation element arranged about the lead body. The fixation element may extend circumferentially about the lead body.

7 Claims, 6 Drawing Sheets

LATERAL FIXATION FOR CARDIAC PACING LEAD

CROSS-REFERENCE TO RELATED APPLICATION this application claims priority to Provisional Application No. 62/658,417, filed Apr. 16, 2018, which is herein incorporated by reference in its entirety.

TECHNICAL FIELD

The present invention relates to medical devices and methods for pacing a patient's heart. More specifically, the invention relates to devices and methods for lead fixation during cardiac pacing.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator (PG) such as a pacemaker, an implantable cardioverter defibrillator (ICD), or a cardiac resynchronization (CRT) device. Such devices are typically coupled to one or more implantable leads having one or more electrodes that can be used to deliver pacing therapy and/or electrical shocks to the heart. Implantable leads can additionally or alternatively be used to stimulate other nervous and/or musculature systems of the body.

To stabilize implantable leads at a target location, the implantable leads may include a fixation mechanism.

SUMMARY

In Example 1, an implantable lead includes: a lead body; an electrode arranged near a distal end of the lead body and extending about a portion of an exterior surface of the lead body; and a fixation element arranged about the lead body and extending circumferentially about the lead body radially adjacent to the electrode and configured to anchor the lead to a tissue wall.

In Example 2, the implantable lead of Example 1, wherein the fixation element is configured to collapse toward the exterior surface of the lead body.

In Example 3, the implantable lead of any one of Examples 1-2, wherein the fixation element is configured to rotate about the lead body to fixate the lead to a tissue wall.

In Example 4, the implantable lead of any one of Examples 1-3, wherein the fixation element is configured to lessen a distance between the electrode and the tissue wall.

In Example 5, the implantable lead of any one of Examples 1-4, wherein the fixation element is coupled to the lead body at a fixed position, and the fixation element is configured to pivot about the fixed position.

In Example 6, the implantable lead of Example 5, wherein a portion of the fixation element extends into a lumen of the lead body at the fixed position.

In Example 7, the implantable lead of Example 6, further comprising a drive mechanism arranged within the lumen of the lead body and coupled to the fixation element, the drive mechanism being configured to control rotation of the fixation element about the lead body.

In Example 8, the implantable lead of Example 7, wherein the drive mechanism includes a nut and a threaded rod, and the drive mechanism is configured to rotate the fixation element about the lead body in response to rotation of the nut.

In Example 9, the implantable lead of Example 8, wherein the drive mechanism includes a safety mechanism configured to stop rotation of the nut and facilitate placement of the fixation element in the tissue wall.

In Example 10, the implantable lead of any one of Examples 8-9, further comprising a stylet configured to pass through the lumen of the lead body and to interact with the drive mechanism to rotate the nut and effect rotation of the fixation element about the lead body.

In Example 11, the implantable lead of any one of Examples 1-10, further comprising a delivery sheath configured to deliver the lead body to a target location and configure to deploy the fixation element, wherein the fixation element is configured to release to a nominal position about the lead body upon deployment from the delivery sheath.

In Example 12, the implantable lead of Example 11, wherein the fixation element comprises a shape memory material, and the fixation element is collapsed against the lead body prior to deployment from the delivery sheath.

In Example 13, the implantable lead of any one of Examples 1-12, wherein the fixation element includes a helical shape angled about the lead body.

In Example 14, the implantable lead of any one of Examples 1-13, wherein the electrode is at least one of level with the exterior surface of the lead body and angled relative to the exterior surface of the lead body.

In Example 15, the implantable lead of any one of Examples 1-14, wherein the electrode is radially focused relative to the lead body and configured to pace a HIS bundle of a patient.

In Example 16, an implantable lead including: a lead body; an electrode arranged near a distal end of the lead body and extending about a portion of an exterior surface of the lead body; and a fixation element arranged about the lead body and extending circumferentially about the lead body radially adjacent to the electrode and configured to rotate about the lead body to anchor the lead to a tissue wall.

In Example 17, the implantable lead of Example 16, wherein the fixation element is configured to collapse toward the exterior surface of the lead body in response to rotation about the lead body.

In Example 18, the implantable lead of Example 16, wherein the lead body is to deploy substantially perpendicular to the tissue wall and the fixation element is configured to lessen a distance between the electrode and the tissue wall in response to rotation about the lead body.

In Example 19, the implantable lead of Example 16, wherein the fixation element includes a helical shape angled about the lead body.

In Example 20, the implantable lead of Example 16, wherein the electrode is at least one of level with the exterior surface of the lead body and angled relative to the exterior surface of the lead body.

In Example 21, the implantable lead of Example 16, wherein the fixation element is coupled to the lead body at a fixed position, and the fixation element is configured to pivot about the fixed position.

In Example 22, the implantable lead of Example 19, wherein a portion of the fixation element extends into a lumen of the lead body at the fixed position.

In Example 23, the implantable lead of Example 22, further comprising a drive mechanism arranged within the lumen of the lead body and coupled to the fixation element, the drive mechanism being configured to control rotation of the fixation element about the lead body.

In Example 24, the implantable lead of Example 16, wherein the electrode is radially focused relative to the lead body and configured to pace a HIS bundle of a patient.

In Example 25, a system including: an implantable lead having: a lead body including an outer tubular portion defining an exterior surface of the lead body, an electrode arranged near a distal end of the lead body, and a fixation element extending circumferentially about the lead body radially adjacent to the electrode; and a drive mechanism being configured to effect rotation of the fixation element about the lead body; and stylet configured to interact with the drive mechanism and control the rotation of the fixation element.

In Example 26, the system of Example 25, further comprising a delivery sheath configured to deliver the lead body to a target location and configure to deploy the fixation element, wherein the fixation element is configured to release to a nominal position about the lead body upon deployment from the delivery sheath.

In Example 27, the system of Example 26, wherein the fixation element comprises a shape memory material, and the fixation element is collapsed against the leady body prior to deployment from the delivery sheath.

In Example 28, the system of Example 25, wherein a portion of the fixation element extends into a lumen of the lead body and the drive mechanism is arranged within the lumen of the lead body and coupled to the fixation element.

In Example 29, the system of Example 28, wherein the drive mechanism includes a nut and a threaded rod, and the drive mechanism is configured to rotate the fixation element about the lead body in response to rotation of the nut.

In Example 30, the system of Example 29, wherein the drive mechanism includes a safety mechanism configured to stop rotation of the nut and facilitate placement of the fixation element in the tissue.

In Example 31, the system of Example 25, wherein the stylet configured to pass through the lumen of the lead body and to interact with the drive mechanism to rotate the nut and effect rotation of the fixation element about the lead body.

In Example 32, the system of Example 25, wherein the fixation element is coupled to the lead body at a fixed position, and the fixation element is configured to pivot about the fixed position.

In Example 33, a method of deploying a lead at a target location, the method including: delivering a lead body to the target location, the lead body including a proximal end and a distal end, and an outer tubular portion defining an exterior surface of the lead body, an electrode arranged near a distal end of the lead body, and a fixation element arranged about the lead body and extending circumferentially about the lead body radially adjacent to the electrode; and rotating the fixation element about the lead body to anchor the lead to a tissue wall and initiate contact between the electrode and the tissue wall.

In Example 34, the method of Example 33, wherein delivering the lead body includes arranging the electrode perpendicular to the tissue wall and rotating the fixation element lessens a distance between the electrode and the tissue wall.

In Example 35, the method of Example 33, wherein rotating the fixation element includes collapsing the fixation element toward the exterior surface of the lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various aspects of the present disclosure are directed toward implantable leads having a fixation mechanism that extends circumferentially, radially, or laterally from a lead body. Fixation mechanisms that protrude from a distal end of the lead in a longitudinal direction may anchor the lead (and electrodes arranged with the lead) perpendicular to the tissue. Aspects of the present disclosure, however, include fixation mechanisms that extend in a radial direction, relative to the lead body, to facilitate fixation of the lead at a target location. In addition, the fixation mechanism may facilitate delivery of the lead at a target location and also enhance the lead/tissue interface.

Figure 1:
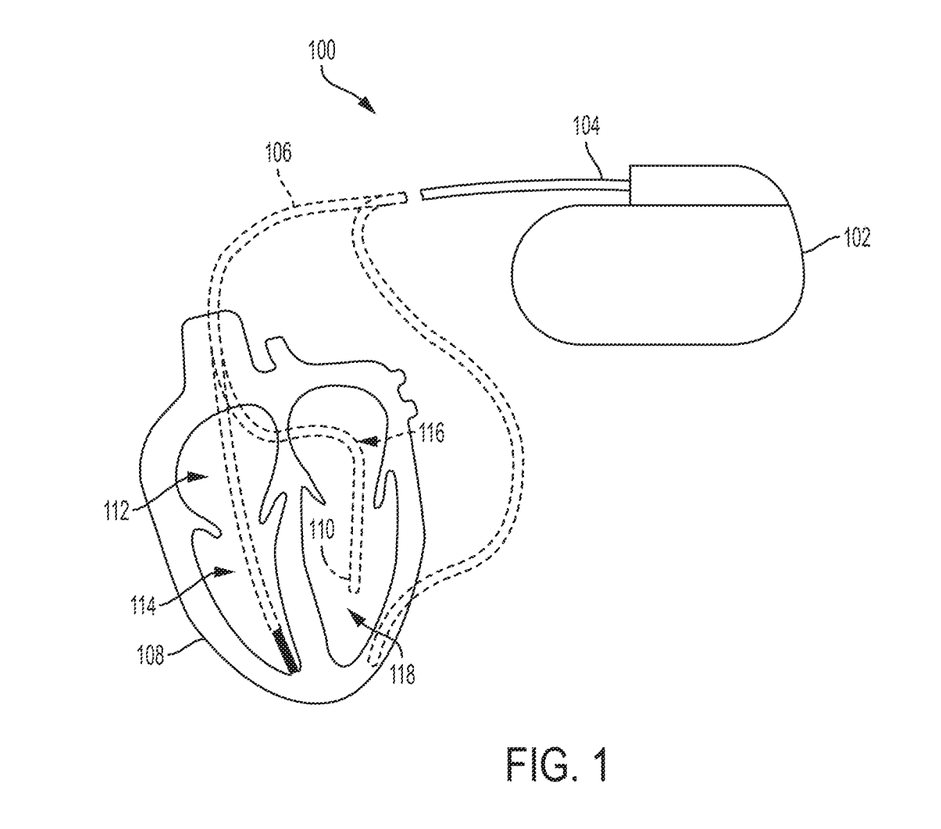
FIG. 1 shows an illustration of an example system that can be used in relation to embodiments of the present invention.

FIG. 1 shows an illustration of an example system 100 that can be used in relation to embodiments of the present invention. The system 100 may include an implantable medical device 102 coupled to lead 104 in accordance with embodiments of the disclosure. The implantable medical device 102 may be an implantable pulse generator and may be used for mapping and/or stimulating a patient's heart 108. The lead 104 may include a lead body 106. The lead 104 may include a number of electrode structures (not shown) arranged on the lead body 106. The electrode structures may be arranged circumferentially about the lead 104. In certain instances, the electrode structures may extend at least partially around the circumference of the lead body 106.

The lead body 106 may include a distal end 110 which is implanted in the patient's heart 108. The distal end 110 of the lead body 106 extend into the patient's heart 108 to a target location. FIG. 1 illustrates the chambers of the heart 108, including a right atrium 112, a right ventricle 114, a left atrium 116, and a left ventricle 118. As shown in FIG. 1, the lead 104 may be arranged at one or more locations in the heart 108. The lead 104, for example, may be delivered to the patient's heart 108 by entering the vascular system through a vascular entry site (not shown) and a superior vena cava to be implanted in the right atrium 112. The lead 104 may be used to stimulate the bundle of His (not shown) at an atrial location proximate to a tricuspid valve in the right atrium 112. This location is proximate to the apex of the triangle of Koch.

The lead 104 may be directly implanted in a tissue wall of the heart 108. In certain instances, the lead 104 may include a fixation mechanism arranged with the lead body 106. As discussed in further detail below, the fixation mechanism may be a lateral fixation mechanism.

Figure 2:
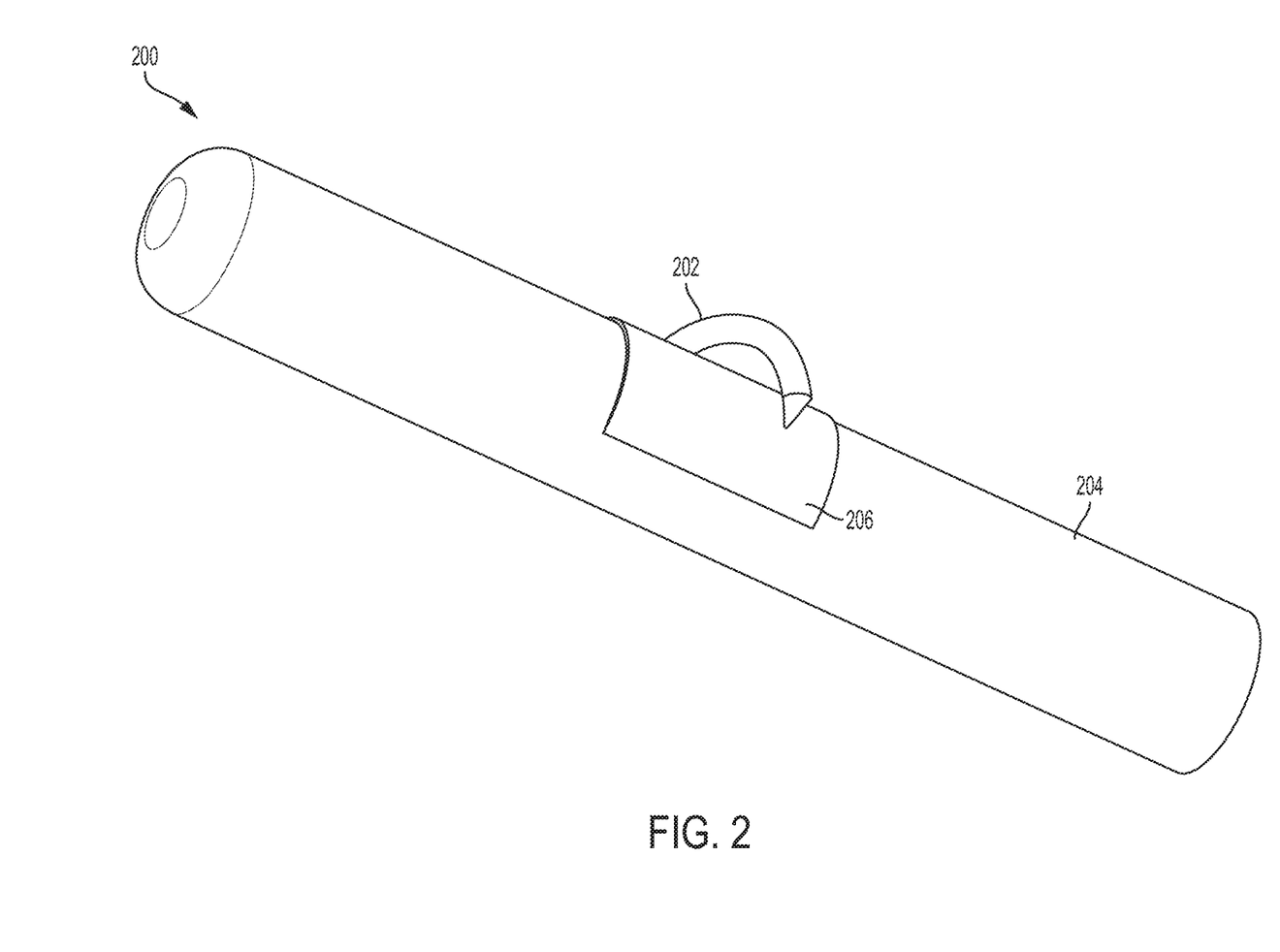
FIG. 2 shows an illustration of an example lead and fixation element that can be used in relation to embodiments of the present invention.

FIG. 2 shows an illustration of an example lead 200 and fixation element 202 that can be used in relation to embodiments of the present invention. More specifically, FIG. 2 shows a distal portion of the implantable lead 200 that may be arranged at and delivered to a target location within or about a patient's heart (as discussed above with reference to FIG. 1). The lead 200 may include a lead body 204 having a proximal end and a distal end, and an outer tubular portion defining an exterior surface of the lead body 204 as shown in FIG. 2. The lead 200 may also include an electrode 206 that extends circumferentially about a portion of the lead body 204.

The fixation element 202, as shown in FIG. 2, may be arranged about the lead body 204 such that the fixation element 202 extend circumferentially about the lead body 204. In certain instances, the fixation element 202 may be arranged in a location or position on the lead body 204 that is radially adjacent to the electrode 206. In addition, the fixation element 202 may be configured to anchor the lead 200 to a tissue wall. The fixation element 202 may be configured to laterally fix the lead body 204 relative to a target location. More specifically and as one example, the fixation element 202 may be arranged within tissue at the target location to press the electrode 206 directly against the tissue. The fixation element 202 allows for the lead 200 to be fixated or anchored in tissue at a location that is directly adjacent to the electrode 206. The fixation element 202 may lessen the potential for improper or undesired stimulation or pacing from the electrode 206 to occur. The lead 200 may shift due to the patient's heart beating, for example, and the fixation element 202 is configured to maintain a position of the electrode 206 relative to the target location.

In certain instances, the lead 200 may be used to stimulate areas of a patient's heart that are difficult to locate. For example, the lead 200 may be used in stimulating the bundle of His due to the relatively small area of the HIS bundle. Directly stimulating the bundle of His can simultaneously pace both the right and left ventricles of the heart, and avoiding pacing induced dyssynchrony. In some other prior art leads, a helical electrode may be used at a distal end of the lead to penetrate the tissue wall and locate the bundle of His. The electrodes of these prior art leads, for example, are arranged away from the point of stabilization in the tissue wall. The electrodes of these prior art leads are proximal of the distal end, where the fixation mechanism is located.

In addition, the fixation element 202 is configured to lessen stress on the tissue wall into which the fixation element 202 is arranged. The lead 200 may move after implantation in response to body movement of the patient or the patient's heart rhythm. The lateral fixation element 202 presses the lead body 204 (and the electrode 206) against the tissue wall such that the lead body 204 facilitates the fixation element 202 stabilization of the lead 200. In addition, the stabilization of the lead 200 in this manner lessens stress on the fixation element 202 and thereby lessens the opportunity for the fixation element 202 to break in the tissue. Movement of a lead can cause shifting of the fixation mechanism which may lead to scar tissue formation. Thus, the lateral fixation element 202 being configured to press the lead body 204 (and the electrode 206) against the tissue wall reduces movement of the lead 200 and lessens the opportunity for scar tissue to form. Thus, the lead 200 and fixation element 202 facilitate interfacing between the electrode 206 and a tissue wall while lessening the opportunity for scar tissue formation thereby improving the performance of the lead 200.

Figure 3:
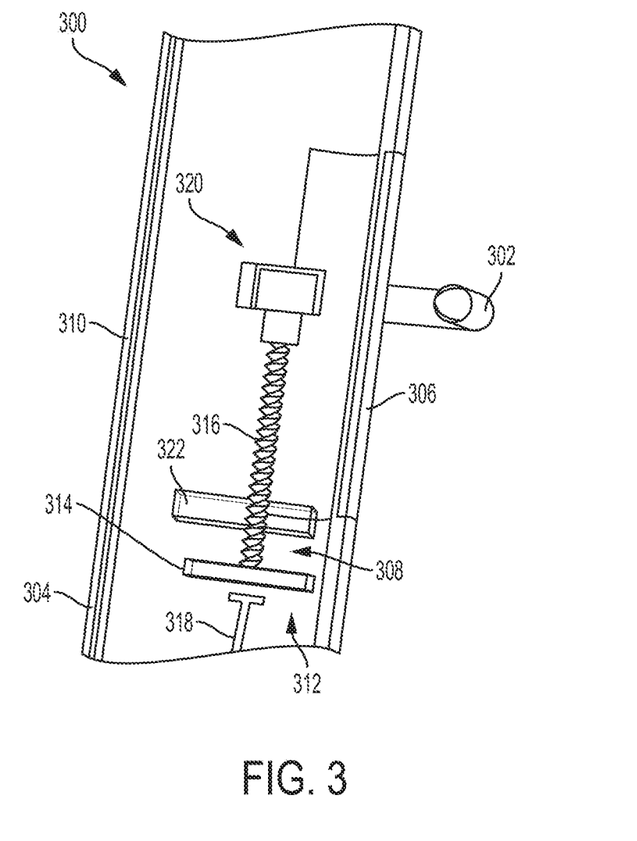
FIG. 3 shows a partial cutaway illustration of an example lead, fixation element, and drive mechanism that can be used in relation to embodiments of the present invention.

FIG. 3 shows a partial cutaway illustration of an example lead 300, fixation element 302, and drive mechanism 308 that can be used in relation to embodiments of the present invention. FIG. 3 shows a distal portion of the implantable lead 300 that may be arranged at and delivered to a target location within or about a patient's heart (as discussed above with reference to FIG. 1). The lead 300 may include a lead body 304 having a proximal end and a distal end, and an outer tubular portion defining an exterior surface 310 of the lead body 204 as shown in FIG. 2. As shown in FIG. 3, the lead 300 may also include an electrode 306 that extends circumferentially about a portion of the exterior surface 310 of the lead body 304.

In addition, the lead 300 includes a fixation element 302 that is arranged about (e.g., laterally) the lead body 304. As shown in FIG. 3, the fixation element 302 extends circumferentially about the lead body 304 radially adjacent to the electrode 306. The fixation element 302 may be configured to rotate about the lead body 304 to anchor the lead 300 to a tissue wall. In certain instances, the fixation element 302 is configured to collapse toward the exterior surface 310 of the lead body 304 in response to rotation of the fixation element 302 about the lead body 304. The fixation element 302, for example, may be rotated by use of a drive mechanism 308. The drive mechanism 308 may be arranged within a lumen 312 of the lead body 304. In addition, the drive mechanism 308 may be coupled to the fixation element 302 and configured to control rotation of the fixation element 302 about the lead body. In certain instances, the drive mechanism 308 includes a nut 314 and a bolt 316 (e.g., a threaded rod).

In certain instances, the nut 314 translates the bolt 316 to effect rotation of the fixation element 302. The nut 314 may be actuated or driven by a user using a stylet 318 (or coil or other similar mechanism). The stylet 318 may be arranged through the lumen 312 of the lead body 304 from a position external to the patient after delivery of the lead body 304 to tissue at a target location (as explained in further detail with reference to FIGS. 6A-B). In certain instances, the stylet 318 may include a screw that interfaces with nut 314, which is removable from the lumen 312 of the lead body 304 after implant, or, in other instances, the stylet 318 may represent a conductor coil that is interfaced with the nut 314 that remains as a part of the lead 300 after implant. A user may engage the stylet 318 with the nut 314 (if the stylet 318 is removable) and rotate the stylet 318 to rotate the bolt 316 (in either instance if the stylet 318 is removable or a non-removable conductor coil).

The bolt 316 is coupled to an interface portion 320 of the fixation element 302 that is arranged internal to the lumen 312 of the lead body 304. The nut 314 translates the bolt 316 within the interface portion 320 of the fixation element 302 to rotate the fixation element 302 about the lead body 304. In certain instances, the stylet 318 may move the interface portion 320 (e.g., toward the exterior surface 310 of the lead body 304 to the lumen 312). The fixation element 302 may be coupled to the lead body 304 at a fixed position with the fixation element 302 being configured to pivot about the fixed position. In certain instances, the fixed position is the location on the lead body 304 at which the fixation element 302 transitions between the exterior surface 310 of the lead body 304 to the lumen 312.

The fixation element 302, in certain instances, may be configured to pivot about the fixed position and press the electrode 306 against a tissue wall. The fixation element 302 is radially adjacent to the electrode 306 and therefore directly facilitates the electrode 306 being pressed against the tissue wall at a target location. The fixation element 302 may be screwed or driven into the tissue wall to fixate and anchor the lead body 304 at the target location. In certain instances, the lead 300 may include a safety mechanism 322 that is configured to stop rotation of the nut 314 and facilitate placement of the fixation element 302 in the tissue. The safety mechanism 322 can stop the fixation element 302 from over-rotating into the tissue. Over-rotation of the fixation element 302 could damage tissue or improperly anchor the lead body 304.

In certain instances and is shown in FIG. 3, the electrode 306 is radially focused relative to the lead body 304. The electrode 306 is configured to deliver stimulating or pacing energy in an oriented manner. The lead body 304 may include a dielectric or other insulative material to facilitate radially focus of the electrode 306. In addition, the fixation element 302 may be a conductive structure that is configured to deliver stimulating or pacing energy. Further and as noted above, the electrode 306 may be configured to pace a HIS bundle of a patient.

Figure 4:
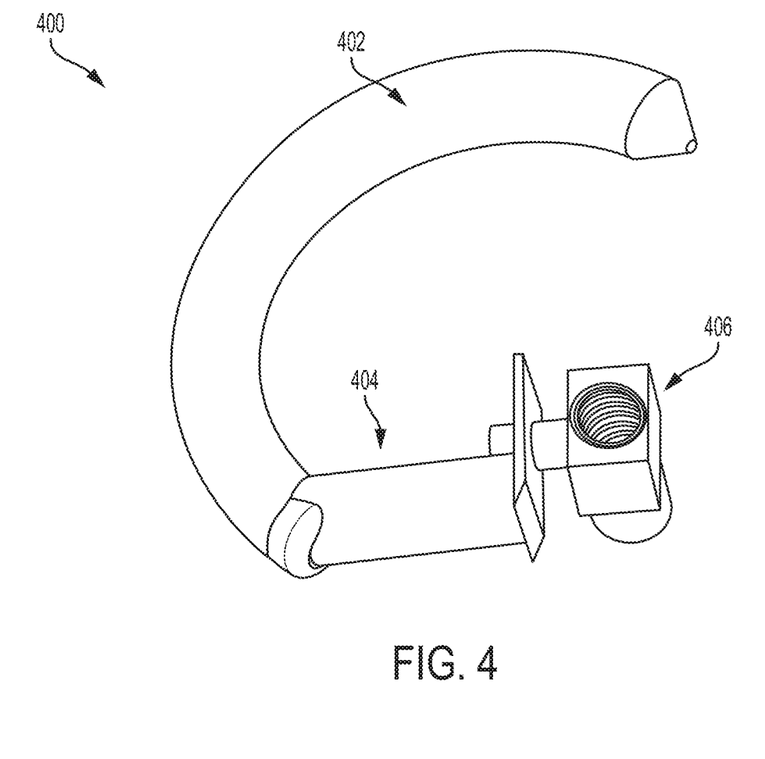
FIG. 4 shows an illustration of an example fixation element that can be used in relation to embodiments of the present invention.

FIG. 4 shows an illustration of an example fixation element 400 that can be used in relation to embodiments of the present invention. The fixation element 400 may include a hook portion 402 that is arranged about a lead body. In addition, the fixation element 400 may include a pivot portion 404 that is arranged internal to the a lumen of the lead body. The pivot portion 404 may be coupled to an adjustable portion 406 that is driven by a drive mechanism as explain in further detail above with reference to FIG. 3.

The adjustable portion 406 may be held stationary while the drive mechanism (not shown) causes the pivot portion 404 to effect rotation of the pivot portion 404. In certain instances, a driver mechanism (such as stylet 318) moves the adjustable portion 406 laterally (e.g., toward an interior surface of lead) to effect movement of the pivot portion 404. The adjustable portion 406 tightens against the interior surface of lead to effect swinging of the pivot portion 404 in certain instances. The adjustable portion 406 can be metallic or non-conductive. In addition, the pivot portion 404 can be effected by having at least a part of the pivot portion 404 being molded or glued into the lead. In certain instances, the adjustable portion 406 causes the pivot portion 404 to rotate within the lumen of the lead and cause rotation of the hook portion 402. In certain instances, certain portions of the hook portion 402 are radiopaque. The hook portion 402 having radiopaque portions allows for visualization of the fixation and anchoring of a lead by a physician.

Figure 5:
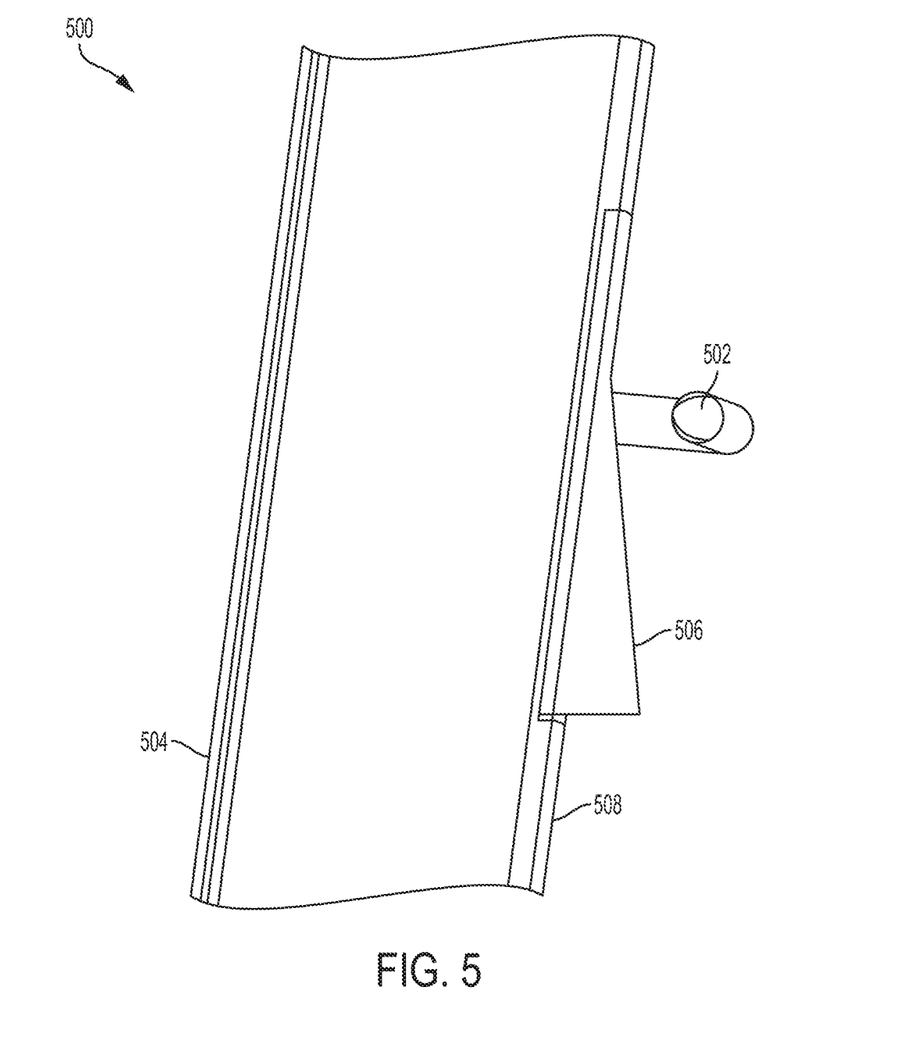
FIG. 5 shows an illustration of another example lead and fixation element that can be used in relation to embodiments of the present invention.

FIG. 5 shows an illustration of another example lead 500 and fixation element 502 that can be used in relation to embodiments of the present invention. FIG. 5 shows a distal portion of the implantable lead 500 that may be arranged at and delivered to a target location within or about a patient's heart (as discussed above with reference to FIG. 1). In addition to the fixation element 502, the lead 500 may include a lead body 504 having a proximal end and a distal end, and an outer tubular portion defining an exterior surface 508. As shown in FIG. 3, the lead 300 may also include an electrode 506 that extends circumferentially about a portion of the exterior surface 508 of the lead body 504.

In addition, the lead 500 includes a fixation element 502 that is arranged about (e.g., laterally) the lead body 504. The fixation element 502 extends circumferentially about the lead body 504 radially adjacent to the electrode 506. As discussed in detail above, the fixation element 502 may be configured to rotate about the lead body 504 to anchor the lead 500 to a tissue wall.

In addition, the electrode 506 may be angled relative to the exterior surface 508 of the lead body 504. The angled electrode 506 may facilitate the interface between tissue and the electrode 506. In certain instances, the fixation element 502 tightens the angled electrode 506 toward the tissue thereby pressing the angled electrode 506 against the tissue.

Figure 6A:
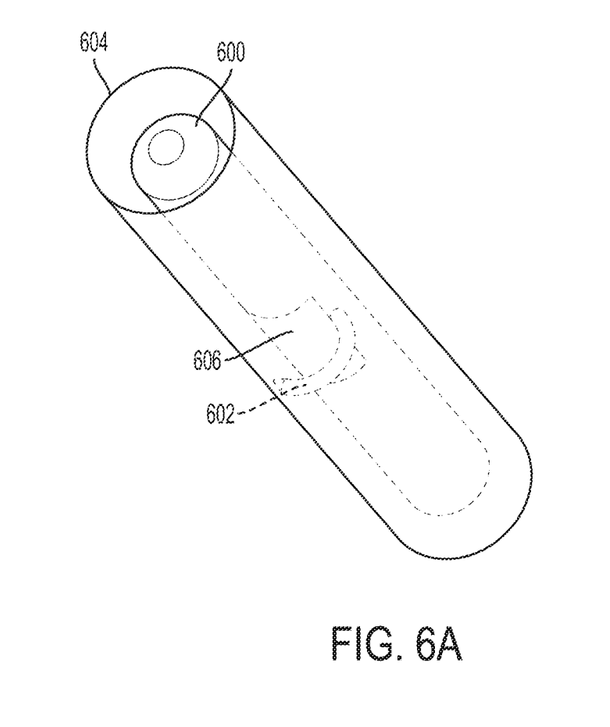
FIG. 6A shows an illustration of an example lead and fixation element within a delivery sheath that can be used in relation to embodiments of the present invention.
Figure 6B:
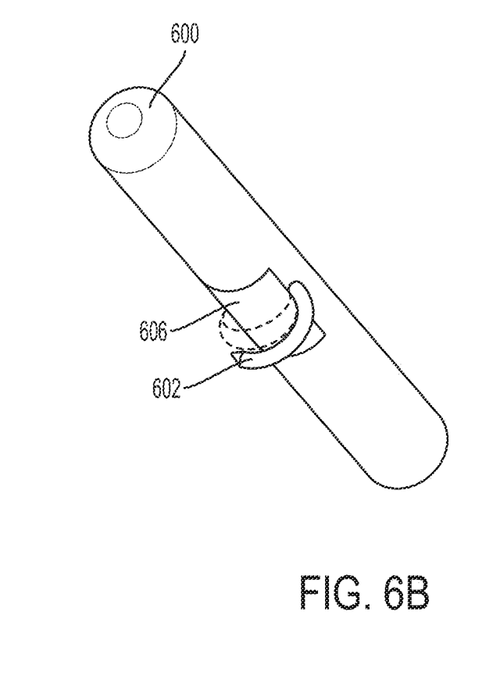
FIG. 6B shows an illustration of the lead and fixation element, shown in FIG. 6A, deployed from the delivery sheath.

FIG. 6A shows an illustration of an example lead 600 and fixation element 602 within a delivery sheath 604 that can be used in relation to embodiments of the present invention. FIG. 6B shows an illustration of the lead 600 and fixation element 602, shown in FIG. 6A, deployed from the delivery sheath 604. The implantable lead 600 may be arranged at and delivered to a target location within or about a patient's heart (as discussed above with reference to FIG. 1). The lead 600 may also include an electrode 606 that extends circumferentially about a portion of the exterior surface 508 of the lead body. In addition, the lead 600 includes a fixation element 602 that is arranged about (e.g., laterally) the lead 600. The fixation element 602 extends circumferentially about the lead 600 radially adjacent to the electrode 606. As discussed in detail above, the fixation element 602 may be configured to rotate about the lead 600 to anchor the lead 600 to a tissue wall.

The delivery sheath 604 may be use in delivering the lead 600 to a target location and deploying the lead 600 at the target location. Rather than using a curved or dual curved delivery mechanism to deliver and angle the lead 600 relative to tissue at the target location, the lead 600 may be deployed from the delivery sheath 604 perpendicular to the tissue at the target location. The fixation element 602 being lateral and radially adjacent to the electrodes 606 allows for delivery and positioning in this manner. The lead 600 and fixation element 602 may be used to pace difficult areas of the heart due to size or location (e.g., the His bundle or right ventricular septal wall).

As noted above, prior art leads have a fixation mechanism at a distal end of the lead body. Thus, the prior art leads are delivered via a delivery catheter with one or more curvatures to orient the distal fixation mechanism relative to the tissue. Positioning the prior art leads in this manner may cause stress against the wall due to torque applied when screwing the distal fixation mechanism into the tissue. The lateral fixation element 602, however, lessens the opportunity for stress applied to the tissue during fixation. As noted above with reference to FIG. 3, the fixation mechanism 602 may be coupled to a drive mechanism that effects rotation of the fixation mechanism 602. The fixation element 602 is configured to lessen a distance between the electrode 606 and the tissue wall in response to rotation about the lead 600.

The fixation element 602 extending circumferentially, radially, or laterally about the lead 600 may anchor the lead 600 (and electrode 606 arranged with the lead) perpendicular to the tissue. The fixation element 602 being lateral relative to the lead 600 presses the lead 600 (and the electrode 606) against the tissue wall such that the lead 600 facilitates the fixation element 602 stabilization of the lead 600. In addition, the stabilization of the lead 600 in this manner lessens stress on the fixation element 602 and thereby lessens the opportunity for the fixation element 602 to break in the tissue.

The fixation element 602 may be configured to spring outwardly relative to the lead 600 after deployment from the delivery sheath 604 as shown comparing FIG. 6A and FIG. 6B. In certain instances, the fixation element 602 may be formed of a shape memory material (e.g., Nitinol) and regain a deployed configuration extending outward from the lead 600 after being collapsed within the delivery sheath 604 as shown comparing FIG. 6A and FIG. 6B.

In certain instances and as shown in dotted lines in FIG. 6B, the fixation element 602 may have a helical shape. The fixation element 602 may be helically arranged about the lead 600. The fixation element 602, in these instances, has a corkscrew-like orientation about the lead 600. In addition, the lead 600 may include multiple fixation elements 602 arranged alone the lead 600 that are configured in the same or similar manner as the fixation element 602.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A system comprising:
an implantable lead comprising:
a lead body including an outer tubular portion defining an exterior surface of the lead body,
an electrode arranged near a distal end of the lead body, and
a fixation element extending circumferentially about the lead body radially adjacent to the electrode; and
a drive mechanism being configured to effect rotation of the fixation element about the lead body, wherein the drive mechanism includes a nut and a threaded rod, and the drive mechanism is configured to rotate the fixation element about the lead body in response to rotation of the nut; and
a stylet configured to interact with the drive mechanism and control the rotation of the fixation element.

2. The system of claim 1, further comprising a delivery sheath configured to deliver the lead body to a target location and configure to deploy the fixation element, wherein the fixation element is configured to release to a nominal position about the lead body upon deployment from the delivery sheath.

3. The implantable lead of claim 2, wherein the fixation element comprises a shape memory material, and the fixation element is collapsed against the leady body prior to deployment from the delivery sheath.

4. The system of claim 1, wherein the implantable lead further comprises a lumen and a portion of the fixation element extends into a lumen of the lead body and the drive mechanism is arranged within the lumen of the lead body and coupled to the fixation element.

5. The system of claim 4, wherein the stylet is configured to pass through the lumen of the lead body and to interact with the drive mechanism to rotate the nut and effect rotation of the fixation element about the lead body.

6. The system of claim 1, wherein the drive mechanism includes a safety mechanism configured to stop rotation of the nut and facilitate placement of the fixation element in the tissue.

7. The system of claim 1, wherein the fixation element is coupled to the lead body at a fixed position, and the fixation element is configured to pivot about the fixed position.

* * * * *